United States Patent
Butler

[11] Patent Number: 6,001,071
[45] Date of Patent: Dec. 14, 1999

[54] AQUATIC EXERCISE AND REHABILITATION DEVICE

[76] Inventor: Brian R. Butler, 2727 Hillview Dr., Broomall, Pa. 19008

[21] Appl. No.: 09/024,970

[22] Filed: Feb. 6, 1998

[51] Int. Cl.[6] .............................. A61H 1/00; A61H 9/00; A63B 23/035; A63B 22/12; A61N 2/00

[52] U.S. Cl. .............................. 601/36; 482/55; 482/62; 482/78; 482/111; 482/145; 601/26; 600/9; 4/494

[58] Field of Search ................................ 482/55, 111, 51, 482/57, 78, 145, 62; 600/9, 13, 15; 601/36, 26; 4/494

[56] References Cited

U.S. PATENT DOCUMENTS

| | | | |
|---|---|---|---|
| 743,373 | 11/1903 | Bachelet | 600/13 |
| 2,419,998 | 5/1947 | Johnson | 601/36 |
| 3,824,993 | 7/1974 | Grant | 601/36 |
| 3,928,219 | 12/1975 | Papay et al. | 508/559 |
| 3,991,749 | 11/1976 | Zent | 601/36 |
| 4,169,591 | 10/1979 | Douglas | 482/58 |
| 4,537,181 | 8/1985 | Shalhoob et al. | 600/9 |
| 4,759,544 | 7/1988 | Diaz | 482/111 |
| 4,918,766 | 4/1990 | Leonaggeo, Jr. | 4/495 |
| 4,976,426 | 12/1990 | Szabo et al. | 482/111 |
| 5,108,088 | 4/1992 | Keller et al. | 482/111 |
| 5,295,929 | 3/1994 | Weisz | 4/495 |
| 5,316,532 | 5/1994 | Butler | 482/111 |
| 5,366,435 | 11/1994 | Jacobsen | 600/13 |
| 5,487,713 | 1/1996 | Butler | 482/111 |
| 5,558,604 | 9/1996 | Hopkins | 482/111 |
| 5,647,826 | 7/1997 | Butler | 482/111 |

FOREIGN PATENT DOCUMENTS

| | | | |
|---|---|---|---|
| 2223053 | 10/1974 | France | 482/57 |
| 8903237 | 4/1989 | WIPO | 482/111 |

*Primary Examiner*—Richard J. Apley
*Assistant Examiner*—Victor Hwang
*Attorney, Agent, or Firm*—Connolly Bove Lodge & Hutz, LLP

[57] ABSTRACT

An aquatic exercise and rehabilitation device includes a cycle assembly mounted in a vessel containing water. The cycle assembly includes a seat and a pivotally mounted handlebar on each side of the seat. A pair of pedals is rotationally mounted with each pedal connected to a respective handlebars by a linkage for transmitting the motion of the handlebars and pedals to each other. The motor drive assembly is connected to the pedals for causing rotation to the pedals.

22 Claims, 2 Drawing Sheets

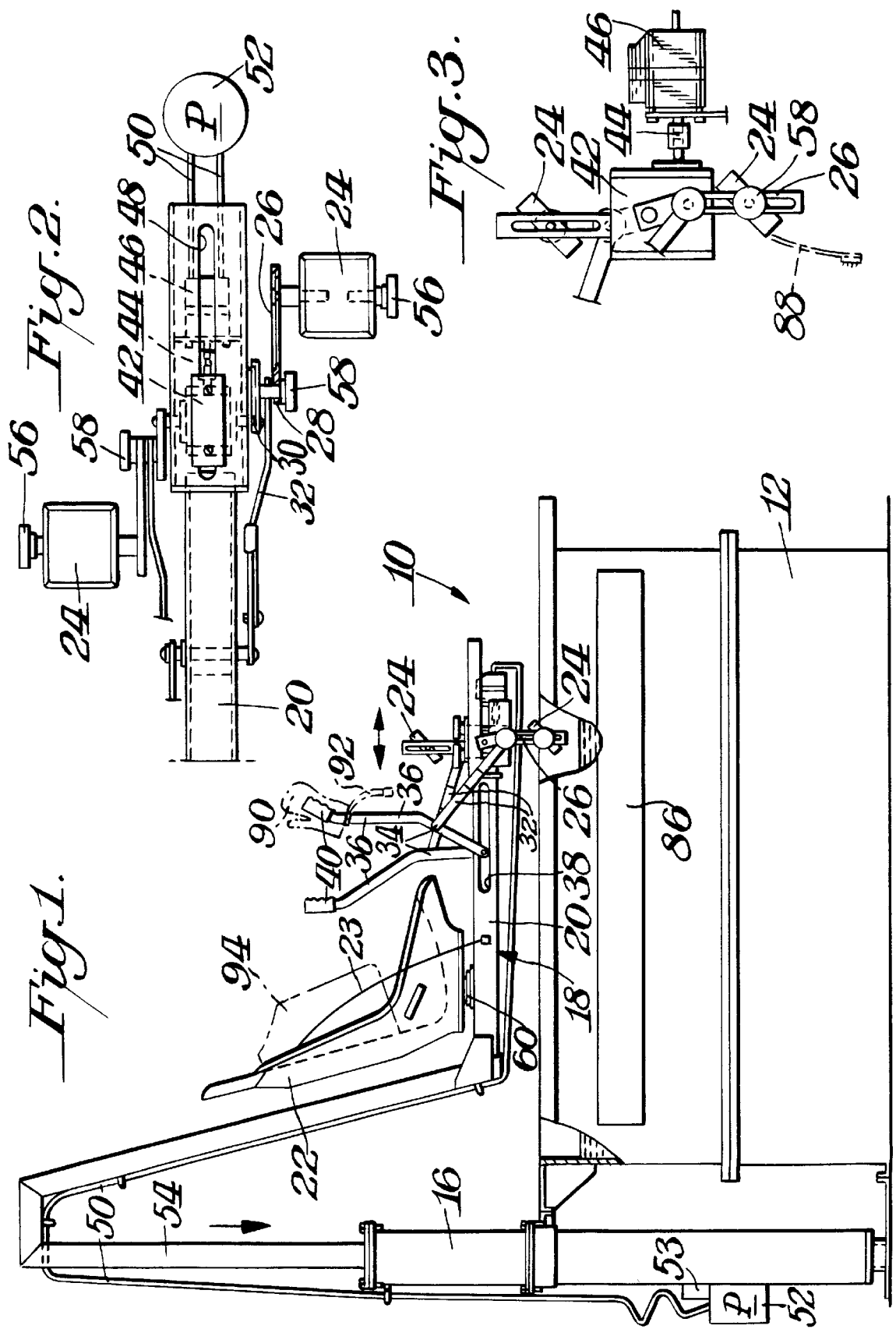

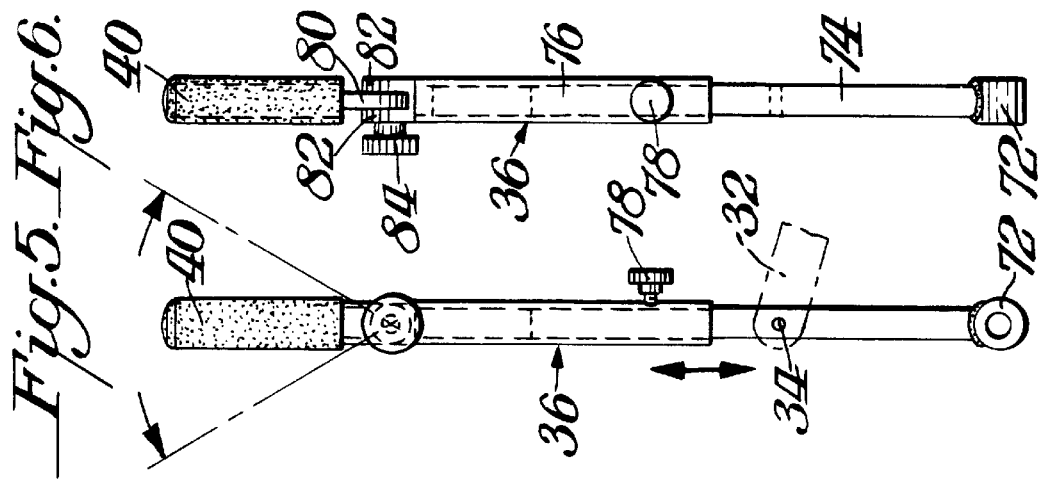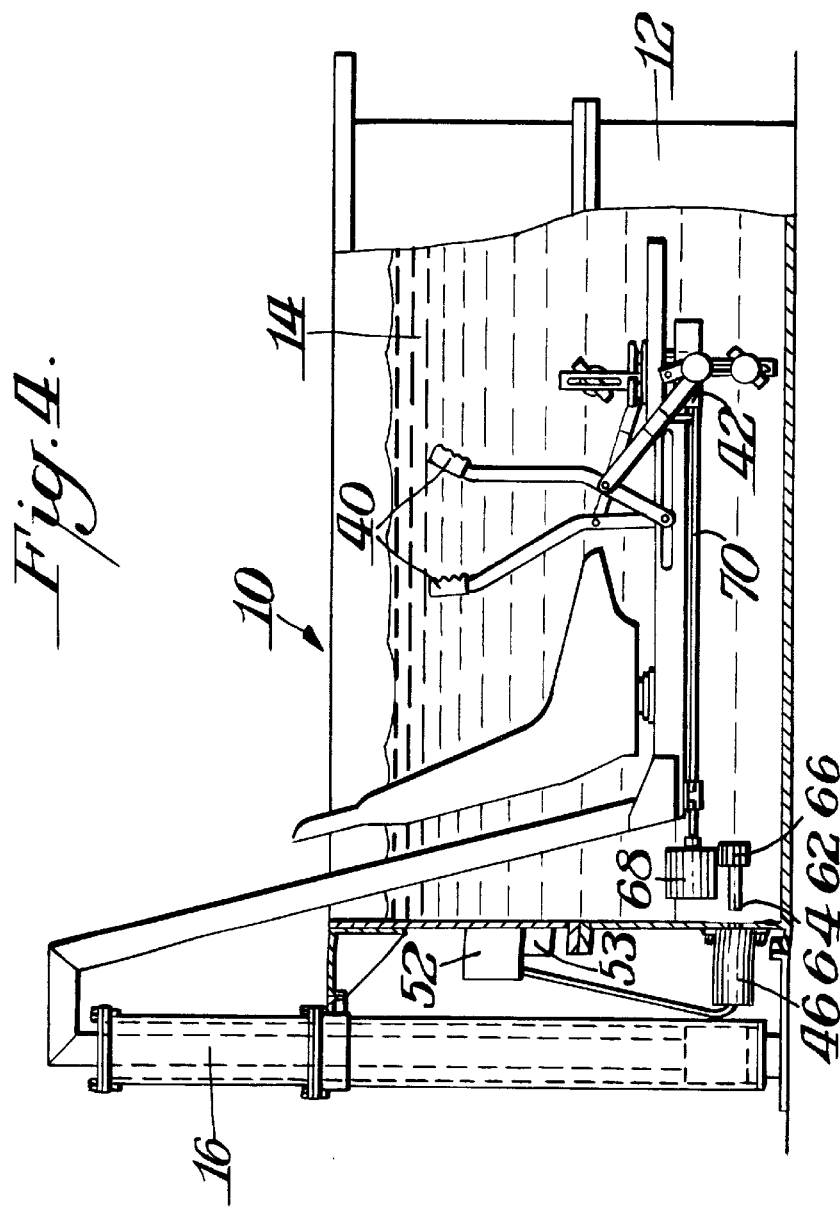

AQUATIC EXERCISE AND REHABILITATION DEVICE

BACKGROUND OF THE INVENTION

An aquatic exercise has been used in particular with unilaterally or bilaterally diminished mobility or range of motion of the upper or lower extremities as well as by amputee as well as by other musculoskelatal and neurologically challenged individuals. A person, for example, is substantially lighter when under water and thus able to perform exercises under water that could not be otherwise performed. Studies on the benefits of aquatic exercise indicate that cardiac volume increases by nearly one-third with emersion to the neck. It has also been established that water exercise could be aerobically efficient. Water helps patients with diseased hearts and those with joint disease as well as patients with hypertension. Aquatic exercise programs have also been beneficial to restore fitness in obese patients. Because of the protective effects against heavy joint loading with such individuals a program may start in water and eventually move to land as the tolerance builds thus achieving effective conditioning and weight loss.

One of the difficulties with aquatic exercise particularly for patients having unilaterally or bilaterally diminished mobility or range of motion is in assuring that the arms and/or legs will move in the desired exercise. My U.S. Pat. Nos. 5,316,532 and 5,487,713 disclose variations in an aquatic exercise and rehabilitation device which includes having interconnected pivoted handle bars and rotatable pedals on an exercise cycle which is lowered into a water containing vessel. With such devices arm movement and foot movement are achieved by rotating the pedals and/or pivoting the handlebars of the device back and forth under power from the user. My U.S. Pat. No. 5,647,826 also discloses variations which include different types of exercise devices in addition to cycles.

SUMMARY OF THE INVENTION

An object of this invention is to provide an aquatic exercise and rehabilitation device which is motorized to assist the user in arm and leg movements.

A further object of this invention is to provide such a device which is of simplified construction having minimal moving parts and which permits the maintenance of the device while the main components are out of the water.

In accordance with this invention an aquatic exercise and rehabilitation device of the type disclosed in my above noted U.S. patents and in co-pending application Ser. No. 08/888,860, filed Jul. 7, 1997 is modified to incorporate a motor for providing the drive to rotate the pedals which in turn are linked to the handlebars so that there is joint pivotal movement of the handlebars. Thus, the device does not depend upon input from the user to provide the moving force.

In a preferred practice of the invention the motor is a hydraulic reversible motor having a neutral position and using vegetable oil as its fluid. In one embodiment the motor itself could be mounted within the vessel directly to the exercise cycle. The hoses from the motor lead to an external pump. In an alternative device the motor is mounted outside of the vessel operatively connected to a drive shaft within the vessel for rotating the pedals.

In a preferred practice of the invention the handlebars of the device are adjustable in length. The seat for the exercise cycle preferably includes a swivel mount. The device might also include various restraint members such as straps and gloves and a vest for assuring that the user's arms and legs are firmly mounted to the pedals and handlebars and the user is securely in the seat thereby assuring the proper exercise benefits.

THE DRAWINGS:

FIG. 1 is a side elevational view of an aquatic exercise and rehabilitation device in accordance with one embodiment of this invention;

FIG. 2 is a fragmental top plan view showing portions of the exercise cycle used in the embodiment of FIG. 1;

FIG. 3 is a fragmental side elevational view showing portions of the exercise cycle of FIGS. 1–2;

FIG. 4 is a view similar to FIG. 1 of an alternative form of device in accordance with this invention;

FIG. 5 is a side elevational view of a modified handlebar structure which could be used with either of the devices of this invention; and FIG. 6 is a front elevational view of the handlebar structure shown in FIG. 5.

DETAILED DESCRIPTION

The present invention is based upon an aquatic exercise and rehabilitation device of the type disclosed in my U.S. Pat. Nos. 5,316,532, 5,487,713, and 5,647,826 and in my U.S. patent application Ser. No. 08/888,860, filed Jul. 7, 1997. All of the details of these patents and application are incorporated herein by reference thereto. In general, such a device could include a lift assembly which would selectively raise and lower an exercise cycle into and out of a treatment vessel containing water. The advantages of such an arrangement include the ability to have the user positioned on the exercise cycle when the cycle is out of water so that assistance is readily available. Additionally, maintenance is facilitated by having the various portions of the exercise cycle accessible out of the treatment vessel.

FIG. 1 shows a device 10 in accordance with one embodiment of this invention. As shown therein device 10 includes a vessel 12 which would contain water 14 or any other suitable liquid. A lift mechanism 16 is operatively connected to an exercise cycle 18 for selectively moving the exercise cycle into and out of the treatment vessel 12 in the manner described in my patents and application.

The exercise cycle 18 generally includes a frame or support 20 on which a seat 22 is mounted. A pair of pedals 24 is provided on the frame remote from seat 22. Each pedal 24 is mounted in a slot in bar 26 as best shown in FIGS. 2–3. Thus, the amount of extension or positioning of pedals 24 from seat 22 can be controlled by adjusting the position of each pedal 24 in the slot of bar 26.

As best shown in FIGS. 2–3 each slotted bar 26 is mounted to a coupling 28 which in turn is rotationally mounted to shaft 30. Thus, the rotation of shaft 30 causes coupling 28 and slotted bars 26 to rotate thereby rotating pedals 24. A link 32 is connected to each coupling 28 with the opposite end of each link 32 connected at an intermediate point 34 to a handle bar 36 pivotally mounted in a slot 38. The handlebars 36 are located at opposite sides of frame 20 as shown in FIG. 1 with each handlebar 36 on a different side of seat 22. Each handlebar 36 terminates at its free upper end in a handle 40.

This manner of interconnection of the pedals 24 and handlebars 36 results in joint rotational movement of the pedals 24 and reciprocal pivotal movement of the handlebars 36 in the manner described in my patents and application except that with the present invention rotation of pedals 24 may be achieved by rotating the shaft 30,30 through the power of a motor rather than relying upon manual power from the user.

Each shaft 30,30 is driven by a worm gear speed reducer 42 connected by coupling 44 to hydraulic motor 46. Motor 46 is mounted to frame 20 by fasteners extending through a slot 48. Thus, device 10 includes adjustability in the distance between the seat 22 and the handlebars 36,36 and pedals 24,24 in a transverse direction by means of the slots 38,48 and adjustability in a horizontal/vertical direction between the pedals 24,24 and the seat by means of the slot in bars 26,26.

Hydraulic motor 46 is provided with a pair of hoses 50 leading to a pump 52. FIG. 2 schematically illustrates the pump 52 to be adjacent to the motor 46. In actual practice of the invention, however, the pump 52 would be located externally of vessel 12, such as shown in FIG. 1, and portions of hoses 50,50 could be of a spiral nature to permit extension and contraction of the hose length in accordance with the raising and lowering of lift mechanism 54. As described in my patents and application the lift mechanism or structure 16 is also a rotating or lateral movement mechanism in that the cycle assembly would be raised or lifted directly above the vessel and then moved completely away from the vessel so that the user could mount the cycle while out of the vessel. The cycle assembly would then be moved back above the vessel (as shown in FIG. 1) and then lowered into the vessel to its operative position (as shown in FIG. 4). Because the user is positioned on the cycle when the cycle is out of the vessel, any necessary adjustments could be made while the cycle is out of the vessel. Similarly, because the motor 46 in FIG. 1 remains operatively connected to the cycle assembly during the various movements of the cycle assembly, the cycle assembly could be operated by the motor at different locations with respect to the vessel including out of the vessel.

The various positioning of the components of cycle 18 can be conveniently adjusted by selectively loosening and tightening the various knobs 56 for the pedals 24 and knobs 58 for the links 32. Knobs (not illustrated) would also be provided at slot 48.

Further adjustability may be achieved by utilizing a swivel mount 60 for securing seat 22 to frame 20. Thus, the position of the user could be adjusted by rotation about the vertical axis of swivel mount 60.

FIG. 4 illustrates a variation of the device 10 wherein the motor 46 is located externally of vessel 12. As shown therein motor shaft 62 extends through a water proof sealed bearing 64 in the wall of vessel 12. Shaft 62 drives a gear 66 which in turn engages a gear 68 at the end of a drive shaft 70. Instead of gears 66,68 friction drive wheels may be used. Drive shaft 70 in turn is connected to worm gear speed reducer 42 to operate the pedals and handlebars in the same manner as in the embodiment of FIGS. 1–3. As is apparent from FIG. 4, when lift mechanism 16 is actuated to raise the cycle assembly, the gear 68 at the end of drive shaft 70 is moved away from and out of engagement with the gear 66 at the end of motor shaft 62. This arrangement thus provides drive connecting structure selectively operatively connecting the motor shaft 62 to the drive shaft 70 when the cycle assembly is lowered into the vessel to an operative position as shown in FIG. 4 and provides for operatively disconnecting the drive shaft from the motor shaft when the cycle assembly is raised above the operative position shown in FIG. 4.

It is to be understood that any suitable power means or motor may be used to drive the pedals and thus cause simultaneous pivotal movement of the handlebars. In the preferred practice of the invention the drive assembly utilizes a motor which is preferably a hydraulic motor that could be speed adjusted in its RPM's such as by valving or by electric current. Preferably, motor 46 is of variable speed. In the preferred practice of the invention the motor is associated with a speed reducer and preferably a worm gear speed reducer. The hydraulic fluid used with the motor drive assembly is preferably vegetable oil which would be safe particularly where the user might have cuts or other exposed sores.

The motor is preferably reversible and has a neutral position. In the neutral position the motor could be disengaged so that a manual power option is available as in my patents for patients with the ability to provide manual power.

The invention may be practiced utilizing various other structures to provide adjustability for the user and to assure that the user achieves effective exercise by having the user's feet and arms moved in response to rotation of the pedals and reciprocal pivoting of the handlebars.

FIGS. 5–6 show a variation of the handlebars 36 which enables the effective length and orientation of the handlebars to be adjusted. As shown therein the base of each handlebar 36 includes a shaft 72 which is pivotally mounted to frame 20. Shaft 72 is secured to an inner member 74 which is telescoped into an outer tubular member 76. Inner member 74 could be hollow but is preferably solid. Link 32 is secured to inner member 74 at pivot pin 34. The telescopic positioning of inner member 74 and outer member 76 may be controlled in any suitable manner. FIGS. 5–6 illustrate the provision of adjustment knob 78 which extends through a hole in outer member 76 for engagement against inner member 74. Thus, knob 78 would be rotated to a loose adjustment position permitting free vertical movement and rotational movement of outer member 76 and inner member 74. When the desired vertical and rotational position is achieved, knob 78 is rotated to its closed locking position. If desired, knob 78 could be actuated by a spring mechanism to urge knob 78 axially to its closed position rather than by a rotational movement. A further alternative would be to provide recesses or holes in inner member 74 which would be penetrated by knob 78. Such arrangement would provide a more positive lock between the inner and outer member 74,76, but would limit the degree of possible positions that could be achieved.

FIGS. 5–6 also illustrate adjustability in the angular orientation of handle 40. As shown therein handle 40 includes a tongue extension 80 disposed between a pair of flanges 82 at the upper end of outer member 76. An adjustment knob 84 extends through aligned holes in flanges 82 and tongue 80. Thus, the angular positioning of handle 40 may be achieved by moving knob 84 to its loose unlocked position thereby permitting free rotation of handle 40. When the desired position is achieved, knob 84 is actuated to its locked position. Such actuation may be by means of a spring urging handle 84 to its locked condition or by means of threaded engagement of handle 84 with a threaded opening in the remote flange 82 or by any other suitable locking structure.

The invention may also be practiced by incorporating any suitable number of magnets 86 at any suitable locations on vessel 12. Such magnets would be desired in accordance with practices where magnetic fields are utilized for therapeutic purposes. As illustrated in FIG. 1 a large elongated magnet 86 would be located so as to be generally in line with the seat or more particularly the user sitting in the seat when cycle 18 is immersed into vessel 12. A corresponding magnet is preferably located on the opposite side wall of vessel 12 in line with magnet 86. Each magnet 86 preferably extends substantially the entire length of vessel or tank 12. The utilization of such magnets as an enhancement to the user is not limited to an aquatic exercise device in the form of a cycle but may also include any other type of exercise devices some of which are discussed in my U.S. Pat. No. 5,647,826. Such other assemblies include, but are not limited to treadmills and horizontal type steppers.

In order to assure that the user's feet remain on pedals 24 straps or other restraints may be utilized in the practice of this invention. FIG. 3, for example, illustrates in phantom a strap 88 which extends from pedal 24 and would be disposed around the calf of the user for keeping the user's legs in line with the pedals. The free end of strap 88 includes fastening elements such as VELCRO to form a closed loop. Alternatively, endless loops or other restraints could be provided on pedals 24 to engage the user's foot. Pedal 24 could, for example, include a shoe or sock secured to the pedal into which the user would insert the user's foot. Preferably a restraint would be provided for each leg/foot. Such strap or restraint could be located at other portions of the cycle 18 such as extending from the frame 20.

If desired, one or preferably both of the handles 40 may be provided with a restraint to assure that the user's hands will remain on the handles 40. FIG. 1, for example, illustrates in phantom a glove in the form of a mitten 90 secured to one of the handles 40. Mitten 90 may have a strap 92 having fastening structure such as hook and loops (VELCRO) to assure a firm mounting of the mitten 90 on the user.

As best illustrated in FIGS. 1 and 4, handles 40 include hand grip indentations which would be particularly desirable where the user is able to wrap the fingers around handle 40.

FIG. 1 also illustrates a vest plate 94 to be secured to seat 22 for wrapping around the front of the user. Alternatively, straps or other restraints could be secured to seat 22 for assuring that the user remains properly positioned in seat 22.

The invention may be practiced with other variations which would be obvious to one of ordinary skill in the art. It is also to be understood that while the invention has been described with particular reference to an exercise cycle, various features of the invention could be practiced with other aquatic exercise devices.

What is claimed is:

1. An aquatic exercise and rehabilitation device comprising a vessel for having water therein, a cycle assembly in said vessel and having an operative position within said vessel, said cycle assembly including a seat mounted to a frame, a pair of pivoted handlebars mounted to said frame, each of said handlebars terminating in a handle at its upper end, each of said handlebars being disposed for being pivotally movable along opposite sides of said seat, a pair of oppositely mounted spaced rotatable pedals, each of said pedals being mounted to a pedal shaft, each of said pedals being connected to a respective one of said handlebars by a linkage for transmitting the motion of said handlebars and said pedals to each other whereby rotational movement of said pedals is transmitted to said handlebars as reciprocal pivotal movement of said handlebars, adjustment structure for adjusting the relative positioning of said seat and said handlebars and said pedals with respect to each other, a motor drive assembly connected to said pedals for causing rotation of said pedals when said motor drive assembly is actuated, said motor drive assembly including a variable speed hydraulic motor, said motor being mounted to said frame at a location between said spaced pedals, said motor being connected to both of said pedal shafts by a single drive connection for jointly rotatingly driving both of said pedal shafts upon actuation of said motor, lifting and lateral movement structure for selectively lifting said cycle assembly above said vessel and laterally moving said cycle assembly away from said vessel to facilitate a user getting on said cycle assembly while said cycle assembly is out of and away from said vessel and for laterally moving said cycle assembly to a position above said vessel and then lowering said cycle assembly back into said vessel, said motor being mounted directly to said cycle assembly for joint movement with said cycle assembly during the lifting and lateral movement and lowering of said cycle assembly, said motor drive assembly including a power source located externally of said vessel, power transmitting members connecting said power source to said motor, said transmitting members being disposed along a path which does not interfere with the vertical and lateral movements of said cycle assembly and a path wherein the vertical and lateral movements of said cycle assembly do not interfere with the transmission of power from said power source to said motor, said motor drive assembly being capable of being operative when said cycle assembly is in different locations with respect to said vessel including in said operative location and including completely out of said vessel, said transmitting members being a pair of hoses leading from said motor to a pump, said pump being said power source, and said hoses being mounted to said lifting and lateral movement structure.

2. The device of claim 1 including a speed reducer mounted between said motor and said pedals.

3. The device of claim 1 wherein said hydraulic motor uses vegetable oil as its fluid.

4. The device of claim 1 including magnets secured to side walls of said vessel.

5. The device of claim 1 including restraints mounted to said cycle assembly for engaging the legs/feet of a user.

6. The device of claim 1 wherein said handlebars are adjustable in length.

7. The device of claim 6 wherein each of said handles is pivotally mounted to said upper end of said handlebar.

8. The device of claim 1 wherein hand restraint structure is mounted to each of said handles.

9. The device of claim 1 including body restraint structure secured to said seat.

10. The device of claim 1 wherein said motor is a reversible motor having a neutral position.

11. The device of claim 1 wherein said seat is mounted to said frame by a swivel mount.

12. The device of claim 1 wherein said handlebars and said motor are horizontally adjustably mounted for movement toward and away from said seat, and said pedals are adjustably mounted toward and away from said seat.

13. An aquatic exercise and rehabilitation device comprising a vessel for having water therein, a cycle assembly in said vessel, said cycle assembly including a seat, a pair of pivoted handlebars, each of said handlebars terminating in a handle at its upper end, each of said handlebars being disposed for being pivotally movable along opposite sides of said seat, a pair of oppositely mounted rotatable pedals, each of said pedals being connected to a respective one of said handlebars by a linkage for transmitting the motion of said handlebars and said pedals to each other whereby rotational movement of said pedals is transmitted to said handlebars as reciprocal pivotal movement of said handlebars, a motor drive assembly connected to said pedals for causing rotation of said pedals when said motor drive assembly is activated, said motor drive assembly including a motor, lifting structure for selectively lifting said cycle assembly out of said vessel to facilitate a user getting on said cycle assembly while said cycle assembly is out of said vessel and for lowering said cycle assembly back into said vessel, said motor being mounted externally of said vessel, said motor including a motor shaft extending through a sealed bearing in a wall of said vessel, a drive shaft within said vessel, said pedals being mounted on a pedal shaft, said drive shaft operatively connected to said pedal shaft for rotating said pedal shaft and said pedals, and drive connecting structure selectively operatively connecting said motor shaft to said drive shaft when said cycle assembly is lowered into said vessel to an operative position and for operatively disconnecting said drive shaft from said motor shaft when said cycle assembly is raised above said operative position.

14. The device of claim 13 including restraints mounted to said cycle assembly for engaging the legs/feet of a user.

15. The device of claim 13 wherein said handlebars are adjustable in length.

16. The device of claim 15 wherein each of said handles is pivotally mounted to said upper end of said handlebar.

17. The device of claim 13 wherein hand restraint structure is mounted to each of said handles.

18. The device of claim 13 including body restraint structure secured to said seat.

19. The device of claim 13 wherein said motor is a variable speed reversible hydraulic motor having a neutral position.

20. The device of claim 13 wherein said cycle assembly includes a frame, and said seat is mounted to said frame by a swivel mount.

21. The device of claim 13 wherein said motor shaft extends through a sealed bearing in a wall of said vessel.

22. The device of claim 21 including a speed reducer between said drive shaft and said pedals.

* * * * *